United States Patent [19]
Pindak et al.

[11] Patent Number: 5,330,897
[45] Date of Patent: Jul. 19, 1994

[54] SIALIC ACID BINDING LECTIN OF PROTOZOAN ORIGIN

[75] Inventors: Frank F. Pindak; David J. Wells, both of Mobile, Ala.; Pavol Demés, Bratislava, Czechoslovakia

[73] Assignee: South Alabama Medical Science Foundation, Mobile, Ala.

[21] Appl. No.: 885,729

[22] Filed: May 19, 1992

Related U.S. Application Data

[63] Continuation-in-part of Ser. No. 626,111, Dec. 14, 1990, abandoned, which is a continuation-in-part of Ser. No. 344,923, Apr. 27, 1989, abandoned.

[51] Int. Cl.$^5$ .................. G01N 33/574; G01N 33/566; G01N 33/567
[52] U.S. Cl. .................... 435/7.23; 435/7.2; 435/7.21; 435/7.24; 435/7.9; 435/7.94; 436/501; 436/63; 436/64; 436/813; 436/827
[58] Field of Search .............. 435/7.2, 7.21, 7.23, 435/7.9, 7.24, 7.94; 436/501, 64, 63, 813, 815, 827; 530/396

[56] References Cited

U.S. PATENT DOCUMENTS 4,520,111  5/1985  Miller .................. 436/501

OTHER PUBLICATIONS

Wells et al., Annual Metting of the American Society for Microbiology, Miami Beach, Florida, U.S.A., May 8–13, 1988. *Abstr. Annu. Meet. Am Soc. Microbiol.*, 88 (1988).
Roth et al., *J. Histochem. Cytochem.*, 32(11):1167–76 (1984). Abstract only.
Lev et al., *Science*, 232:71 (1986).
Demes et al., *Parasitol Res.*, 75:589–94 (1989).
Pindak et al., *J. Clin. Microbiol.*, 25(4): 609–14 (1987).
Pindak et al., *J. Clin. Microbiol.*, 26(8):1460–63 (1988).
Shibuya et al., *J. Biol. Chem.*, 262(4):1596–1601 (1987).
Shibuya et al., *Archives of Biochem. and Biophys.*, 254(1):1–8 (1987).
Mattern et al., *Am. J. Trop. Med. Hyg.*, 29(1):26–30 (1980).
Kobiler et al., *Infection and Immunity*, 29(1):221–25 (1980).
Kobiler et al., *Am. J. Trop. Med. Hyg.*, 30(5):955–59 (1981).
Sata et al., *J. Histochem. Cytochem.*, 37(11):1577–88 (1989).
Babal et al., *Modern Pathology*, 5:117A, Abstract No. 694 (Jan. 1992).

*Primary Examiner*—Toni R. Scheiner
*Attorney, Agent, or Firm*—Sterne, Kessler, Goldstein & Fox

[57] ABSTRACT

The present invention concerns lectins isolated from the genus Tritrichomonas which bind specifically to sialic acid. The invention further pertains to uses of such lectins, and to processes for their preparation. The invention is further drawn to neuraminidase, particularly from *T. mobilensis*.

10 Claims, No Drawings

SIALIC ACID BINDING LECTIN OF PROTOZOAN ORIGIN

This application is a continuation-in-part of pending U.S. application Ser. No. 07/626,111 filed Dec. 14, 1990, now abandoned, which is a continuation-in-part application of U.S. application Ser. No. 07/344,923 filed Apr. 27, 1989, now abandoned, which disclosures are herein incorporated in their entirety.

BACKGROUND OF THE INVENTION

1. Field of the Invention

The present invention, in the areas of microbiology and immunology, relates to a novel lectin with binding specificity toward sialic acid, to methods of its production and isolation, and to its uses in diagnosis and treatment of diseases. The lectin may be isolated from Tritrichomonas species.

2. Description of the Background Art

The discovery of microbial lectins has opened new approaches for studies of host-parasite interactions. These carbohydrate-specific molecules appear to play an important role in cell recognition and cell adhesion (Liener et al., *The Lectins. Properties, Functions and Applications in Biology and Medicine*, Academic Press, New York (1986)). Many species of bacteria as well as some viruses produce lectins (Mirelman (ed.), *Microbial Lectins and Agglutinins: Properties and Biological Activity*, Wiley, New York (1986)). Very few lectins from parasitic protozoa have been characterized extensively. These include *Giardia lamblia* (Farthing et al., *Infect. Immun.* 51:661-667 (1986): Lev et al., *Science* 232:71-73 (1986); Lev et al., In: Mirelman (ed.) *Microbial Lectins and Agglutinins: Properties and Biological Activity*, Wiley, New York (1986)) and *Entamoeba histolytica* (Kobiler et al., *Infect. Immun.* 29:211-225 (1980); Mirelman et al., In: Mirelman (ed.), *Microbial Lectins and Agglutinins: Properties and Biological Activity*, Wiley, New York (1986); Rosales-Encina et al., *J. Infect. Dis.* 156:790-797 (1987)).

Sialic acid is a carbohydrate produced by both prokaryotic and eukaryotic cells. Due to the ubiquity of sialic acid on the surface of cells of prokaryotic as well as eukaryotic origin, and the presence of sialic acid on a large proportion of glycoproteins in the serum of mammals and in other biological fluids, a stable lectin with high affinity for sialic acid would be of great utility for purposes of diagnosis and therapy of a large variety of diseases.

Many types of carcinomas produce specialized glycoproteins, the majority of which are sialoglycoproteins (Sharma et al., *Indian J. Pathol. Microbiol.* 30:317 (1987)). Among the large variety of human carcinomas producing high molecular weight sialoglycoproteins, such as mucins, human metastatic colon carcinoma cells were found to produce 4 tumor-associated sialoglycoproteins (Irimura et al., *J. Cell. Biochem.* 37:1 (1988)). Various tumors have higher concentrations of sialic acid on their surface than do normal cells, and some tumors secrete polysialic acid (Roth et al., *Amer. J. Pathol.* 133:227-240 (1988); Echenique et al., *Urology* 32:397-400 (1988); Ravindranaths et al., *J. Biol. Chem.* 263:2079-2086 (1988)).

Surface sialic acid expression in the form of sialogangliosides is also characteristic of tumors, such as melanoma (Cheresh et al., *Proc. Natl. Acad. Sci. USA* 82:5155-5159 (1985)); see for review: Dyatlovitskaya et al., *Biochim. Biophys. Acta* 907:125-143 (1987)).

Direct and indirect approaches exist for localization of sialic acid in tissues. In indirect procedures, tissues are processed in parallel with and without neuraminidase digestion to remove sialic acid. Tissues are then stained based on surface negative charge, with reagents such as, for example, colloidal iron hydroxide (Gasic et al., *J. Cell. Biol.* 19:223 (1963)) and cationized ferritin (Danon et al., *J. Ultrastruct. Res.* 38:500 (1972). Comparison of tissue bearing, and denuded of, sialic acid is then made, in order to determine the localization of sialoglycoproteins. These procedures are of limited specificity.

A number of lectins have been shown to have some specificity for terminally sialylated glycoproteins. Wheat germ agglutinin used in conjunction with its succinylated derivatives has been used to localize sialic acid on colon tissue in a relatively nonspecific manner (Moore et al., *Amer. J. Pathol.* 131:477 (1988)).

Sialic acid-specific lectins have been isolated from the hemolymph of several horseshoe crabs, *Limulus polyphemus* (Marchalonis et al., *J. Mol. Biol.* 32:453 (1968)) and *Carcinoscorpus rotunda* (*Biochim. Biophys. Acta* 623:89 (1980)) as well as from lobster and sponge. Of these, only the Limulus lectin is commercially available. This lectin is of very high molecular weight, has a tendency to dissociate (Marchalonis et al., *J. Mol. Biol.* 32:453 (1968)), and is quite expensive ($100/mg; Sigma Chemicals, Catalog).

In addition, a large number of viruses have hemagglutinin activity which is based on apparent binding to sialic acid (Mirelman (ed.), *Microbial Lectins and Agglutinins: Properties and Biological Activity*, Wiley, New York (1986)). None of these is commercially available.

Miller (U.S. Pat. Nos. 4,457,865 and 4,520,111) disclosed a sialic acid specific lectin from the slug *Limax flavus*. This is the only marketed lectin reagent which has been tested for its utility in detecting sialic acid on cells and tissues. For example, Roth et al. (*J. Histochem. Cytochem.* 32:1167-1176 (1984)) used the *Limax flavus* lectin to investigate the distribution of sialic acid in rat pancreas, liver, and colonic mucosa, using fetuin-gold to visualize the tissue-bound lectin. However, the slug lectin is difficult to isolate, expensive, and more importantly, its availability is limited by the organism from which it is derived, since the supply of slugs is limited and depends on unpredictable factors such as weather.

A plant lectin isolated from the bark of the elderberry (*Sambucus nigra L.*), termed SNA (EY Scientific, San Mateo, Calif.), binds to sialic acid linked to either galactose or N-acetyl galactosamine, in an α2-6 linkage (Shibuya et al., *J. Biol. Chem.* 202:1596-1601 (1987)). This lectin has been used to affinity purify glycoproteins, oligosaccharides, and glycopeptides possessing the appropriate disaccharide sequence (Shibuya et al., *Arch. Biochem. Biophys.* 254:1-8 (1987)), although it was found that lectin binding was lost when branching side chains existed at the O-3 position of the penultimate N-acetyl galactosamine residue. This property may limit the usefulness of this lectin.

In summary, very few useful reagents are available in large quantities and at reasonable cost which can serve as sufficiently specific agents to identify, characterize, or even treat tumors on the basis of cell surface sialic acid expression. Therefore, the need for a sialic acid-specific lectin of microbial origin which can be produced economically in large quantities, which is stable, specific, and of high affinity, is well-recognized in the art.

Furthermore, isolation and characterization of sialic acid binding lectin(s) from protozoa would be of benefit in our understanding of the pathobiology of parasite-host interactions. Such a lectin in appropriate pharmacologic form could be employed to modify adherence of the protozoa to host tissues, thereby disrupting infection by Tritrichomonas species. Production of monoclonal antibodies against these trichomonad lectins would provide both diagnostic and therapeutic tools for parasitology.

SUMMARY OF THE INVENTION

This invention comprises a lectin derivable from trichomonad protozoans which binds specifically to sialic acid. The invention additionally comprises methods for purification of this lectin, and methods of use of the lectin. The lectin of this invention is used to purify sialic acid containing molecules such as sialoglycoproteins. In addition the lectin is used to detect the presence of sialic acid on cells and tissues, and to detect the presence of sialic acid or sialic-acid containing molecules in biological fluids. The lectin of this invention, either alone or conjugated to drugs and toxins, is used to diagnose and treat tumors. The lectin in appropriate pharmacologic forms can be employed to treat trichomonad infection by modifying adherence of the protozoa to host tissues, thereby disrupting the pathogenic process. A vaccine preparation of the lectin can be used to induce anti-protozoal immunity. Furthermore, antisera and monoclonal antibodies specific for the sialic acid binding lectin are useful as diagnostic and therapeutic tools for trichomonad infection.

The invention is also drawn to a neuraminidase isolated from *T. mobilensis*. The neuraminidase releases terminal sialic acid residues from glycoproteins, glycolipids and oligosaccharides.

DESCRIPTION OF THE PREFERRED EMBODIMENTS

Lectins are proteins or glycoproteins which bind specifically to sugars (Ofek et al., *Infect. Immun.* 56(539-547 (1988)). Recently, a new species of trichomonad, *Tritrichomonas mobilensis*, isolated from the gastrointestinal tract of the squirrel monkey (*Saimiri sciureus*), was described (Culberson et al., *J. Protozool.* 33:301-304 (1986); Pindak et al., Am. J. Primatol. 9:197-205 (1985)). These trichomonad organisms and their related species are inhabitants of mucosal surfaces (*T. mobilensis*—monkey gastrointestinal; *T. foetus*—bovine urogenital; and *T. augusta*—reptilian gastrointestinal) (Brady et al., *Am. J. Primatol.* 14:65-71 (1988); Honiberg, *Parasitic Protozoa*, Vol. 2, Academic Press, New York (1978); Pindak, et al., *Am. J. Primatol.* 9:197-205 (1985)). In such mucosal sites, sialic acid is one of the major carbohydrates in the mucin glycoproteins (Doehr, In *The Glycoconjugates*, Vol. 1, Horowitz et al. (eds.), Academic Press, New York (1977); Horowitz, *The Glycoconjungates*, Vol. 1, Academic Press, Inc., New York (1977)).

Though the pathogenicity of mammalian trichomonads in the natural host and experimental models has been described (Bunton et al., *Vet. Pathol.* 20:491-494 (1983); Honiberg, *Parasitic Protozoa*, Vol. 2, Academic Press, New York (1978); Pindak, et al., *Am. J. Primatol.* 9:197-205 (1985)), the virulence determinants are unknown. Sialic acid binding molecules are probably important determinants of recognition, just as they are in viruses, mycoplasma and plasmodia (Liener et al., *The Lectins. Properties, Functions and Applications in Biology and Medicine*, Academic Press, New York (1986)). Furthermore, sialoglycoprotein binding molecules can act as cytotoxic substances (Lushbaugh et al., *J. Infect. Dis.* 139:9-17 (1979); Mattern et al., *Am. J. Trop. Med. Hyg.* 20:26-30 (1980)).

The presence and basic properties of a hemagglutinin in the culture fluid of *Tritrichomonas mobilensis* has been reported (Pindak et al., *J. Clin. Microbiol.* 25:609-614 (1987); Pindak et al., 87*th Annu. Meet., Amer. Soc. for Microbiol.* B235:64 (1987)). Inhibition studies using specific sugars revealed that this hemagglutinin is a lectin specifically inhibited by sialic acid (Wells et al., Abstr: 88*th Annu. Meet. Am. Soc. for Microbiol.* (1988)). This Tritrichomonas sialic acid binding lectin, its purification, and its uses, are the subject of this invention.

This invention is directed to lectins of protozoan origin which bind specifically to the sugar, sialic acid (alternatively known as N-acetyl neuraminic acid). In one embodiment, the invention is directed to a sialic acid-binding lectin from the parasitic protozoans known as trichomonads. In a preferred embodiment, the lectin is isolated and substantially purified from *Tritrichomonas mobilensis*. In other embodiments, the lectin is derived from other Tritrichomonas species including, but not limited to, *Tritrichomonas foetus* and *Tritrichomonas augusta*.

The invention is also directed to a "functional derivative" of the intact lectin molecule isolated from the protozoa. Such functional derivatives may be obtained by enzymatic cleavage or chemical fragmentation of the intact lectin molecule. Alternatively, molecular cloning techniques, well known in the art, can be utilized to prepare recombinant forms of the intact lectin or a functional derivative, in which amino acid residues are intentionally added, deleted, or substituted.

The term "functional derivative" of the lectin is intended to refer to "variants" and "chemical derivatives" of the lectin. A "variant" lectin is a lectin which contains any polypeptide subset of the intact lectin molecule and which retains the function of binding to sialic acid. A "chemical derivative" of the lectin is a lectin modified to contain one or more chemical groups (i.e. methyl, acetyl, halogen, phosphate, etc.) Such chemical derivatives may be prepared, by addition of various chemical groups by methods well known in the art.

In one embodiment of this invention, affinity chromatography is used to isolate the lectin. This technique utilizes immobilized molecules carrying one or more sialic acid residues, which interact with the lectin binding site, thereby immobilizing the lectin, which is subsequently eluted. In a preferred embodiment, the high molecular weight sialoglycoprotein, mucin, is used as the affinity partner. In other embodiments, other high or low molecular weight saccharides, glycoproteins, or glycolipids are used. In another embodiment, Concanavalin-A sepharose is used to purify the sialic acid binding lectin, apparently through binding to a mannose residue on the lectin. In yet another embodiment, CIBACRON BLUE 3GA is used as an affinity matrix to purify the sialic acid binding lectin.

In another embodiment, the lectin of this invention is used as an affinity probe to isolate and purify sialic acid containing proteins or other sialylated macromolecules from complex mixtures. The methods of affinity chromatography are well known in the art and are described in Dean et al. (Dean et al., (eds.) *Affinity Chromatography: A Practical Approach*, IPR Press, Oxford, 1985), which is hereby incorporated by reference.

In another embodiment, the lectin of this invention is used to bind to tumor cells containing surface sialic acid. In this embodiment, the lectin can be employed in conjunction with histochemical methods to stain cell or tissue preparations. Histochemical and cytochemical techniques are well known in the art. The use of lectins in such techniques has been described by Damjanov (Damjanov, *Lab. Invest.* 57:5-20 (1987)), which reference is hereby incorporated by reference. In one embodiment, fetuin conjugated to colloidal gold is used to reveal the presence of the Tritrichomonas lectin which has bound to a tissue or cell preparation. In another embodiment, an antibody to the lectin can be coupled to detectable labels and used to detect the binding of the lectin to cell or tissue preparations.

While the lectin is generally discussed in terms of sialic acid binding, it is recognized that nonsialic acid binding of the lectin may occur. Likewise, lectin associated staining may not be based on sialic acid binding.

Detectable labels that can be used in the practice of this invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc.

Examples of suitable non-radioactive isotopic labels include $^{157}$Gd, $^{55}$Mn, $^{162}$Sy, $^{52}$Tr, $^{56}$Fe, etc.

Examples of suitable fluorescent labels include an $^{152}$Eu label, a fluorescein label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to lectins or their functional derivatives, or to antibodies, can be accomplished using standard techniques commonly known to those of ordinary skill in the art. Typical techniques are described by Kennedy, J. H., et al. (*Clin. Chim. Acta* 70:1-31 (1976)), and Schurs, A. H. W. M., et al. (*Clin. Chim. Acta* 81:1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

By the term "histological preparation" is intended any preparation of tissue or cells that is in condition for incubation with the lectin of this invention. Such preparations, well known in the art of histology and cytology, include, but are not limited to frozen sections, paraffin sections, thin plastic sections, cell smears, cytocentrifuge preparations, and cell pellets.

Types of cells which can be detected by, or isolated with, the lectin of this invention include but are not limited to bacteria, protozoa, and other eukaryotic cells such as mammalian lymphocytes and tumor cells. In particular, high sialic acid content is associated with human colon cancer cells and cells of Wilm's Tumor, for which the lectin of this invention may serve as a preferred diagnostic tool.

Different classes of lymphocytes can be also be distinguished by their surface glycolipid content (including sialogangliosides) (Stein et al., *J. Immunol.* 120:676-684 (1978)). Thus, in one embodiment of this invention, the sialic acid binding lectins can be used to identify or isolate lymphocytes based on the presence of such sialylated cell surface structures.

In another embodiment, the lectins of this invention are used to fractionate hemopoietic cells based on surface sialic acid content, as has been done using lectins specific for other sugars (Reisner et al., *Recent Advances in Bone Marrow Transplantation*, pp 355-387, Alan Liss, NY, 1983). Such fractionated hemopoietic cells, from human bone marrow or fetal liver, for example, are then used to reconstitute patients in need of such treatment. Examples of such patients are individuals having diseases including, but not limited to, leukemia, aplastic anemia, severe-combined immunodeficiency, etc.

Antibodies which recognize the Tritrichomonas lectins are prepared by immunizing animals with the purified lectins of this invention, or with whole trichomonads. Polyclonal antisera, containing antibodies to the lectin are obtained from such immunized animals.

In a preferred method, the antibodies of the present invention are monoclonal antibodies (or hapten binding fragments thereof). Such monoclonal antibodies can be prepared using hybridoma technology (Kohler et at., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)). See also, U.S. Pat. Nos. 4,609,893; 4,713,325; 4,714,681; 4,716,111; 4,716,117; and 4,720,459. In general, such procedures involve immunizing an animal (preferably a mouse) with the novel lectin of the present invention (or one of its functional derivatives). The mouse splenocytes are fused with myeloma cells to produce hybridomas, which are subsequently screened for production of monoclonal antibodies to the lectin. Such screening may employ assays of direct binding to the lectin molecule, the inhibition of hemagglutination by trichomonads, or inhibition of lectin binding to sialic acid. Burgess et al. (*Exper. Parasitol.* 62:266-274 (1986)) describe the production of monoclonal antibodies to *T. foetus*, which is hereby incorporated by reference.

The novel lectins (and their functional derivatives) of the present invention may be obtained by natural processes (such as, for example, by recovering the lectin from a protozoan, fungus, bacteria, animal, plant, etc., or by synthetic methods such as, for example, by proteolysis, or by using the Merrifield method for synthesizing polypeptides, or by employing recombinant DNA technologies. The choice of which method to employ will depend upon factors such as convenience, desired yield, etc. It is not necessary to employ only one of the above-described methods, processes, or technologies to produce any of the lectins of the present invention; the above-described processes, methods, and technologies may be combined in order to obtain a particular desired lectin.

In an additional embodiment, the lectin of this invention is used as a vaccine, to immunize animals against Tritrichomonas infections. The presence of the lectin on the surface of trichomonads provides a target for either antibody-mediated or cell-mediated immunity in the host. Such immunization is especially useful for treating *T. mobilensis* infection which is common in primate colonies, and accounts for decreased breeding capacity of various monkey species in captivity. Similarly, such a lectin-based vaccine against *T. foetus* is useful for treating bovine infections which lead to foetal loss.

Another embodiment of the invention is drawn to a neuraminidase, particularly a neuraminidase from *T. mobilensis*. Neuraminidase activity can be detected and purified from culture medium containing *T. mobilensis*. Best results are obtained from whole culture of *T. mobilensis* grown in GMP medium. See Culberson et al. *J. of Protozoology* 33:301-304 (1986).

The neuraminidase can be isolated from the culture medium by purification methods known in the art, for example, affinity chromatography. See Cuatrecasas, P., et al., *Biochem. Biophys. Res. Commun.* 44:178-184 (1971). See also, Harth et al. *Proc. Natl. Acad. Sci. USA* 84:8320-8324 (1987).

Having now generally described the invention, the same will be more readily understood through reference to the following examples which are provided by way of illustration, and are not intended to be limiting of the present invention, unless specified.

EXAMPLE 1

Sialic Acid Binding Lectins in Tritrichomonas Species

Screening for the presence of lectins in cells of *T. mobilensis*, and in four additional trichomonad species (*Tritrichomonas foetus, Tritrichomonas augusta, Trichomonas vaginalis* and *Pentatrichomonas hominis*) revealed that sialic acid binding lectins are present only in flagellates belonging to the genus Tritrichomonas. These lectins may play a role as adhesins (adhesion molecules) in these protozoa.

A. MATERIALS AND METHODS

1. Protozoa and culture conditions

*T. foetus* (ATCC 30003), *T. augusta* (ATCC 30077), and *P. hominis* (ATCC 30000) were obtained from American Type Culture Collection. *T. vaginalis* (NYH 286) was obtained from J. F. Alderete of the University of Texas, San Antonio. *T. mobilensis*, Strain 4190, was isolated from a rectal swab of a captive squirrel monkey in the Primate Research Laboratory of the University of South Alabama (Pindak et al., J. Clin. Microbiol. 25:609-614 (1987)). Axenisation of this isolate was achieved by three transfers in agar-free Diamond TYM (Trypticase-yeast extract-maltose) medium (Diamond, *J. Parasitol.* 43:488-490 (1957)), pH 7.2, supplemented with 10% horse serum and antibiotics (1000 μg/ml penicillin, 1000 μg/ml streptomycin, 400 μg/ml kanamycin and 5 μg/ml Fungisone). After axenisation (verified by standard microbiological tests), cultures were grown in TYM medium supplemented with penicillin-streptomycin (100 U/ml and 100 μg/ml respectively). All other trichomonad species were grown in this modified TYM medium with a modification in the initial pH of the medium for *T. vaginalis* to 6.2. The cultures were maintained in 16×25 mm screw-cap polystyrene tubes or tissue culture flasks at 37° C., or at 27° C. for *T. augusta*.

2. Preparation of Cell Suspensions and Cell-free Lysates

Protozoa were harvested during the late log phase (24-48 hr cultures) by centrifugation at 4° C., 800×g, for 10 rain and were washed three times with 10 mM phosphate buffered saline, pH 7.2 (PBS). Washed protozoal cells were lysed by three cycles of rapid freezing and thawing. The lysate was centrifuged at 1000×g at 4° C. for 20 min and the supernatant filtered through a 0.45 μm Gelman acrodisc filter. The protein content in filtered lysates was determined and the samples were then aliquoted and frozen (−20° C.).

3. Testing of Hemagglutinating (HA) Activity of Cell Lysates

The standard HA assay, described for the *Entamoeba histolytica* lectin (Rosales-Encina, et al., *J. Infect. Dis.* 156:790-797 (1987)) was performed in Falcon #3911 microtiter U plates using serial two-fold dilutions. Equal volumes (25 μl) of serially diluted cell lysates and PBS were mixed before addition of 25 μl of a 2.5% suspension of human type O erythrocytes in PBS prepared as described previously (Pindak et al., *J. Clin. Microbiol.* 25:609-614 (1987)). Hemagglutinin titers were determined after incubation for 1 hr at room temperature and expressed as the reciprocal of the highest dilution which gave a positive reaction.

4. Inhibition by Carbohydrates

For testing the effect of carbohydrate-containing inhibitors on HA activity of lysates or live trichomonads, two HA units of the preparation were used. An HA unit was defined as the amount of agglutinin in the highest dilution showing positive reaction. Carbohydrates and sialoglycoproteins (purchased from Sigma Chemicals) were dissolved in PBS (phosphate buffered saline) and if necessary their pH adjusted to 7.2 with 0.1M NaOH. The inhibitor (25 μl) was mixed with 25 μl of agglutinin and the mixture was incubated for 15 min at room temperature. Thereafter, 25 μl of a 2.5% suspension of erythrocytes were added and the plates incubated and read as above. All inhibitory studies were performed no less than four times.

5. Adherence of Trichomonads to Erythrocytes

The rosette formation assay commonly used with human lymphocytes, which had been applied to studies of *Entamoeba histolytica* adhesions (Ravdin et al., *J. Exp. Med.* 152:377-390 (1980)) was employed as follows. One hundred μl of trichomonas suspension ($2 \times 10^5$ cells) in PBS was mixed with an equal volume of $1 \times 10^7$ human erythrocytes in microcentrifuge tubes. The mixture was centrifuged (400×g, 5 min) and incubated for 1 hr at 4° C. Cell pellets were disrupted by repeated aspiration and the percentage of trichomonads with three or more adherent erythrocytes (rosettes) was determined microscopically.

B. RESULTS

1. HA Activity of Trichomonad Lysates

Cell-free lysates of five trichomonad species were adjusted to the same protein concentration and tested for their ability to agglutinate human erythrocytes. The presence of HA substances was observed in preparations derived from three Tritrichomonas species (*T. mobilensis, T. foetus* and *T. augusta*) but not in similarly prepared material from *T. vaginalis* or *P. hominis*. The trichomonad organisms used in this study had approximately the same amount of agglutinin on their surface based on microscopic examination.

2. Effect of Carbohydrates and Glycoproteins on Tritrichomonas Hemagglutinin

To evaluate whether agglutinin present in lysates of trichomonads is a lectin, inhibition studies were performed with 11 different carbohydrates. The results (Table 1) show that HA reactions by each type of trichomonad was specifically inhibited by N-acetylneuraminic (or sialic) acid. The inhibitory capacity of sialic acid against *T. foetus* was markedly less than with *T. mobilensis* and *T. augusta* hemagglutinins.

The specificity of Tritrichomonas lectin for sialic acid was confirmed by effective inhibition of HA using glycophorin (a major sialoglycoprotein of erythrocyte membranes) and by three other sialoconjugates—fetuin, orosomucoid and bovine submaxillary mucin (Table 2). Asialoglycophorin, lacking the sialic acid, was not inhibitory at a 50-fold higher concentration than an inhibitory concentration of unmodified glycophorin.

3. Adherence of Trichomonads to Human Erythrocytes

The capacity of live trichomonads to bind human erythrocytes was studied in order to determine whether the protozoal lectin was membrane-bound. We found that erythrocytes formed rosettes, with erythrocytes binding to, and surrounding, *T. foetus* cells, and to a lesser extent, *T. mobilensis* organisms. The remaining three strains of trichomonads did not adhere to erythrocytes under these conditions.

The whole-cell trichomonad-erythrocyte hemagglutination reaction was inhibited again by sialoconjugates but not with asialoglycophorin (Table 3) indicating a surface location of sialic acid-specific lectin in these parasites.

TABLE 1

Inhibitory Effect of Carbohydrates on HA Activity of Tritrichomonas Cell-free Lysate
Conc. (µg/ml) required to inhibit 2 HA units

| Carbohydrate | T. mobilensis | T. foetus | T. augusta |
|---|---|---|---|
| D-glucose | >200 | >200 | >200 |
| D-galactose | >200 | >200 | >200 |
| D-fucose | >200 | >200 | >200 |
| D-mannose | >200 | >200 | >200 |
| D-arabinose | >200 | >200 | >200 |
| D-xylose | >200 | >200 | >200 |
| D-fructose | >200 | >200 | >200 |
| Sucrose | >200 | >200 | >200 |
| N-acetylgalactosamine | >200 | >200 | >200 |
| N-acetylglucosamine | >200 | >200 | >200 |
| N-acetylneuraminic acid | 5 | >200 | 10 |

TABLE 2

Inhibitory Effect of Sialoglycoproteins on HA Activity of Tritrichomonas Cell-free Lysates
Conc. (µg/ml) required to inhibit 2 HA units

| Inhibitor | T. mobilensis | T. foetus | T. augusta |
|---|---|---|---|
| Glycophorin | 10 | 10 | 10 |
| Asialoglycophorin | 500 | 500 | 500 |
| Orosomucoid | 150 | 150 | 150 |
| Bovine submaxillary mucin | 60 | 60 | 40 |
| Fetuin | 100 | 60 | 100 |

TABLE 3

Inhibition of HA by Live Cells of *T. foetus* with Sialoglycoproteins

| Inhibitor | Conc. (µg/ml) required to Inhibit 2 HA Units |
|---|---|
| Glycophorin | 10 |
| Asialoglycophorin | 500 |
| Fetuin | 60 |
| Bovione submaxillary mucin | 125 |
| Orosomucoid | 500 |

Although approximately the same amount of lectin was present in cell lysates of the three Tritrichomonas species, its surface disposition varied between species, as was observed microscopically. Additional strains of each species should be studied to permit definitive conclusions about the presence and properties of lectins on the surface membrane of these flagellates.

The precise biochemical relationship of the sialic acid-binding lectins from the three Tritrichomonas species is unknown. The variable inhibition of hemagglutination of the different species' lectins by free sialic acid (Table 1) suggests that the molecular properties may be different in different species.

The observation that "clustered" sialic acid (in the form of sialoglycoproteins) produced more effective inhibition of Tritrichomonas lectins than did free sialic acid is similar to findings with sialic acid specific lectins from invertebrates (Goldstein, I. J., et al., In *The Lectins: Properties, Functions and Applications in Biology and Medicine*, Academic Press, New York (1986)) and microorganisms (Liener, I. E., et al., *The Lectins. Properties, Functions and Applications in Biology and Medicine*, Academic Press, New York (1986)).

EXAMPLE 2

Purification and Partial Characterization of a Sialic Acid Binding Lectin from *T. mobilensis*

The objective of this present study was to isolate and characterize the substances responsible for protozoal-host adhesion directly from the organisms. In this report we describe the purification and partial characterization of a sialic acid binding lectin from *T. mobilensis*.

A. MATERIALS AND METHODS

1. Reagents and Supplies

Bovine submaxillary mucin Type 1-S, N-acetylneuraminic acid Type VI, and additional carbohydrates tested for inhibitory activity as well as all proteases were obtained from Sigma Chemical Company. The sialidase inhibitor, 3-dehydro-2-desoxy-N-acetylneuraminic acid, was obtained from Boehringer Mannheim. Triton X-100 was obtained from Calbiochem. Sepharose 4B was purchased from LKB/Pharmacia. Reagents for SDS polyacrylamide gel electrophoresis (SDS-PAGE) were as follows: Ammonium persulfate, N,N-methylene-bisacrylamide, acrylamide, glycerol, 2-mercaptoethanol, and bromophenol blue were ultrograde from Pharmacia/LKB. Sodium dodecyl sulfate (SDS) and Coomassie brilliant blue R were from Sigma. Electrophoresis purity TEMED was from Biorad Laboratories. Dialysis was performed using Spectra/por 2 (Spectrum Medical Industries) with a cut off of 12 to 14 kilodaltons (kD).

All solutions and buffers were prepared from reagent grade chemicals and deionized, distilled water. PBS is 10 mM phosphate containing normal saline, pH 7.2.

2. Protozoa and Culture Conditions

*T. mobilensis,* strain 4190 isolated in this laboratory., was cultivated as described in Example 1.

3. Purification of Protozoal Lectin

All steps were conducted at 4° C. Frozen pellets prepared as described above were quickly thawed and diluted with 10 ml of cold extraction buffer (PBS containing 0.1% Triton X-100) per ml of packed cellular suspension. After vortexing for 30 sec, extracts were pooled (CELL EXTRACT) and centrifuged at 16,000 rpm, for 60 min, using a Beckman Type 30 rotor. The supernatant (CENTRIFUGATION SUPERNATANT) was concentrated ten-fold using an Amicon YM-100 filter. The retentate was rediluted with extraction buffer and reconcentrated two or more times to remove any contaminating proteins which could pass through the filter (molecular weight cut-off of 100 kD). The initial filtration flow-through was saved for examination (YM-100 INITIAL FLOW-THROUGH). The retentate (YM-100 CONCENTRATE) could be stored at −20° for up to four months or immediately subjected to affinity chromatography as described below.

Bovine submaxillary mucin-sepharose 4B affinity matrix was prepared according to the procedure of Miller (Miller, *Methods in Enzymology* 128:527–536 (1987)). A column with a length/diameter ratio of approximately 6.0 was equilibrated with PBS containing 0.1% Triton X-100 and 0.5M NaCl (washing buffer). Ultrafiltration concentrate as described above was adjusted to 0.5M final NaCl concentration using a 5.0M NaCl stock solution. A sample containing 50 mg of protein and 500,000 HA units was added per ml of packed column volume to the column at a flow rate of 20 ml/hr/cm$^2$. The eluate was monitored spectrophotometrically at 280 nm with the base line adjusted against washing buffer. After addition of sample indicated by an absorbance drop to base-line, the flow-through material was pooled (AFFINITY COLUMN FLOW-THROUGH) and the column was washed with 10 column volumes of washing buffer. HA activity was eluted with 12.5 mM N-acetyl neuraminic acid in washing buffer (elution buffer). Although the majority of HA activity was eluted in the first few ml, 10 to 30% additional activity could be recovered by incubating the column overnight (equilibrated with elution buffer) followed by elution using 2 column volumes of elution buffer. Eluate containing U.V. absorbing material at 280 nm was pooled and dialyzed for 48 hours against two changes of PBS-0.1% Triton (SIALIC ACID ELUTION). The affinity purified lectin was stored for up to four weeks at 4° C. or could be stored frozen without loss of activity.

4. Hemagglutinin Assay

Hemagglutination was measured as described in Example 1, above.

5. Inhibitor studies

For testing the effect of inhibitors on HA activity carbohydrates and glycoproteins were dissolved in PBS and the pH adjusted to neutrality with 0.1M NaOH. Twenty-five μl of serially-diluted potential inhibitor was mixed with 2 units of hemagglutinin preparation contained in 25 μl of PBS. The mixture was incubated for 15 minutes at room temperature and 25 μl of 2.5% suspension of erythrocytes added. Plates were scored as described above. The minimal inhibitory concentration (MIC) was defined as that concentration of inhibitor in the last well with a negative HA response.

6. SDS-Gel Electrophoresis

Samples in the denaturing buffer; with or without mercaptoethanol; were electrophoresed on 1.5 mm slab gels by a modification of the method of Laemmli (*Nature* 227:680 (1970)).

7. Measurement of Sialidase activity

Free sialic acid release from bovine submaxillary mucin was used to determine enzymatic activity. Sample to be tested (total volume 50 μl) was mixed with 250 μl of 0.1M acetate, pH 5.0 and 200 μl of 1% mucin in water. After incubation at 37° for 30 minutes, 0.5 ml of 5% phosphotungstic acid in 2.5N HCl was added with vortexing. Assay tubes were centrifuged at 2000×g for 10 minutes, and 250 μl of the supernatant was assayed for sialic acid by the thiobarbituric acid method (Warren, *J. Biol. Chem.* 234:1971–1975 (1959)). Activity was calculated as μmoles of sialic acid released during a 30 min incubation at 37°. Controls were identical samples precipitated by phosphotungstic acid before the 37° incubation.

B. RESULTS

1. Purification of Lectin

Previous studies demonstrating inhibition of whole protozoal adherence to mammalian cells in culture or erythrocytes by sialoglycoproteins or free sialic acid indicated a membrane location for proposed adhesions and provided the rationale for the purification scheme summarized in Table 4. Non-ionic detergents are useful for solubilizing membrane proteins. Inclusion of 0.1% Triton X-100 in the extraction buffer resulted in total lysis of the organisms and subsequent solubilization of 8–10 fold more lectin than that obtained by freeze-thawing methods used previously. Multiple extractions with Triton-buffer proved unnecessary provided a 10:1 (v/v) ratio of initial extraction buffer to packed protozoal cell pellet was maintained. Low speed centrifugation (2000×g) of this detergent extract followed by a resuspension of the pellet in fresh extraction buffer revealed little or no remaining hemagglutinin activity. Therefore, extracts were pooled and centrifuged in the ultracentrifuge to remove cell debris and insoluble residue before ultrafiltration.

The filtration step provides a convenient means of concentrating the extract as well as eliminating low molecular weight contaminants, though contaminating sialidase activity was not eliminated as shown in Table 4. A very low but detectable amount of HA activity repeatedly observed in the initial YM-100 filter flow-through was not further characterized. Flow-through material tested following the second and third redilution contained no measurable HA activity indicating that low molecular weight agglutinins were not being been generated in the retentate during the concentration process. The total amount of lectin (yield) in the final concentrate was often higher than that in the cell extract fraction. An increase in total HA activity has been reproducibly observed at this step, which may either reflect assay variation or elimination of inhibitors of agglutination.

Mucin-sepharose affinity chromatography has been used in the purification of a sialic acid specific lectin from the slug Limax flavus (Miller, *Methods in Enzymology,* supra). Following repeatedly low yields of the slug lectin, it was found that 0.3N NaCl in the elution buffer improved the recovery. We therefore performed the affinity chromatography under similar high ionic strength conditions also minimizing possible binding of contaminating proteins based solely on the ion exchange properties of affinity matrix. For the *T. mobilensis* lectin, the presence of Triton in the elution buffer does not inhibit binding of lectin to the matrix. In fact, total HA activity eluted from the column is decreased in the absence of 0.1% Triton-X100 from the sialic acid elution buffer. Other methods of lectin release which did not succeed include elution with 0.1M acetate; pH 4.0; 0.1M NaHCO$_3$, pH 9.0; or 0.1M EDTA. Use of sialic acid solutions more concentrated than 12.5 mM did not result in release of additional HA activity either in the initial eluate or that from the 12-hour incubation. Yields corresponded roughly to one mg of lectin from $2.5 \times 10^9$ organisms.

TABLE 4

Hemagglutination Activity, Protein, and Sialidase Activity in Fractions Obtained for the Isolation of Sialic Acid Binding Lectin from *T. mobilensis*[a]

| | | HA Activity | | | | Sialidase Activity | |
|---|---|---|---|---|---|---|---|
| Fraction[b] | Total Prot. (mg) | Spec. Act. (units/mg × 10$^3$ Prot.) | Total Units[c] (units × 10$^5$) | Recovery (%) | Purif. Factor | Spec. Act (m Units/m g Prot.) | Total[d] Activity (Units) |
| Cell Extract | 413 | 2.25 | 9.29 | 100 | 1.0 | 5.11 | 2.11 |
| Centrifugation Supernatant YM-100 Filt. | 342 | 2.43 | 8.43 | 89.7 | 1.1 | 5.60 | 1.92 |
| Flow-thru | 163 | 0.02 | 0.018 | — | — | 2.7 | 0.44 |
| Concentrate Affinity Column | 100 | 9.72 | 9.72 | 104 | 4.33 | 14.1 | 1.41 |
| Flow-thru | 69.8 | 0 | — | — | — | 18.6 | 1.30 |
| Sialic Acid Elution | 0.96 | 889 | 8.60 | 92.6 | 395 | — | — |

[a]Standardized for $2.5 \times 10^9$ cells
[b]Fractions defined in section 3 above
[c]Maximal HA dilution × total volume/0.025
[d]Calculation based on molar extinction coefficient for N-acetylneuraminic acid in cyclohexanone of 57,000 (see section A-7 above).

2. Determination of Lectin Carbohydrate Binding Specificity

The results of studies examining carbohydrate-mediated lectin binding are summarized in Table 5. Out of a total of 24 compounds tested, only neuraminic acid or its derivatives could inhibit HA activity. All other carbohydrates failed to demonstrate any inhibitory activity at concentrations of 100 mM or less. Two methyl esters of sialic acid and a 2,8-linked sialic acid dimer had no or minimal inhibitory activity at the 100 mM level or less.

When glycoproteins and proteins were tested for inhibition of lectin-mediated hemagglutination (Table 6), it was found that only sialoglycoproteins were capable of significant inhibition. Importantly, when their asialo- analogs were tested, inhibitory activity decrease by 3-200 fold.

3. Physical properties

The MW and subunit structure of affinity purified lectin was examined by SDS-PAGE. Under denaturing conditions with mercaptoethanol and SDS, multiple protein bands were observed, both migrating at a relative MW (Mr) above the myosin standard (206 kD). A faintly staining low MW band may represent mucin contamination since the same banding pattern is exhibited when a mucin sample in denaturing buffer is electrophoresed under the same conditions.

Ultrafiltration results of the *T. mobilensis* lectin indicate that HA activity is almost quantitatively retained by the 100 kD cut-off filtration membrane.

TABLE 5

Inhibitory Effects of Carbohydrates on *T. mobilensis* Lectin-Mediated Hemagglutination

| Carbohydrate | Minimal Inhibitory Conc. (mM) |
|---|---|
| Glucose | >100 |
| Mannose | >100 |
| Galactose | >100 |
| Fucose | >100 |
| Maltose | >100 |
| Sucrose | >100 |
| Xylose | >100 |
| Arabinose | >100 |
| Fructose | >100 |
| N-acetylgalactosamine | >100 |
| N-acetylgulcosamine | >100 |
| N-acetyl-β-D-mannosamine | >100 |
| N-acetylmuramic acid | >100 |
| D-galacturonic acid | >100 |
| Mannose-6-phosphate | >100 |
| mannose-1-phosphate | >100 |
| glucuronic acid | >100 |
| N,N-diacetyl chitobiose | >100 |
| Sialic Acid or Derivative | |
| N-acetylneuraminic acid (= sialic acid) | 2.0 |
| 2,3-dehydro-2-deoxy-N-acetylneuraminic acid | >100 |
| 3'-sialyllactose | 2.0 |
| 6'-sialyllactose | 1.0 |
| N-glycolylneuraminic acid | 8.3 |
| N-acetylneruaminic acid β-methyl glycoside | >100 |
| N-acetylneuraminic acid methyl ester, β-methyl glycoside | >100 |

Gangliosides GM1, GM3, GD1A, GD16 did not inhibit the hemagglutination at 3 mg/ml concentrations.

TABLE 6

Inhibitory Effects of Glycoproteins on *T. mobilensis* Lectin-Mediated Hemagglutination

| Glycoprotein or Protein | Minimal Inhibitory Conc. (μg/ml) |
|---|---|
| Mucin | 0.65 |
| Asialomucin | 13.0 |
| Fetuin | 8.33 |
| Asialofetuin | 26.0 |
| Glycophorin | 0.42 |
| Asialoglycophorin | 83.3 |
| Laminin | 6.8 |
| Bovine Albumin | >1000 |
| Avidin | >1000 |
| Lysozyme | >1000 |
| Egg Albumin | >1000 |

TABLE 6-continued

Inhibitory Effects of Glycoproteins on *T. mobilensis* Lectin-Mediated Hemagglutination

| Glycoprotein or Protein | Minimal Inhibitory Conc. (μg/ml) |
|---|---|
| Fibronectin | >333 |

Gel permeation chromatography by HPLC using a SYNCHROPAC GFC-300 column indicates a high molecular weight aggregate greater than 1000 kD.

SDS gel electrophoresis using sample dissolving buffer without mercaptoethanol results in retention of the purified lectin in the stacking gel. In the presence of mercaptoethanol, two high MW bands >200 kD were observed. Taken together these results point to a high MW aggregate composed of subunits of MW>200 kD. These subunits appear to be attached, in part, by disulfide bonds.

C. DISCUSSION

*T. mobilensis* has different attachment characteristics than other enteric protozoa, such as Giardia and Entamoeba. Carbohydrate inhibition studies clearly demonstrate that the Tritrichomonas lectin described here has high affinity for sialic acid and not galactose, mannose, glucose or their derivatives. Furthermore, inhibitory results with purified lectin are in complete agreement with those obtained for cell-culture derived material. These observations taken together are evidence for the identity of the affinity purified lectin and the media derived lectin. This conclusion is supported by studies using monoclonal antibodies.

Perhaps the most striking characteristic of *T. mobilensis* lectin is its temperature stability and resistance to proteolytic enzymes. Samples containing HA activity at an phases of purification have been incubated at 25° C. for up to 24 hours without loss of activity. The heat stability of the affinity-purified lectin is identical to that reported for the media-derived lectin. Little loss of HA activity occurs after 3 hr. at 55° C. and prolonged heating at 70° C. is required for lectin inactivation. In proteolytic digestion studies with trypsin type III, protease type XIV, subtilisin type VIII, alpha-chymotrypsin type I-S, and proteinase K type XXVIII; only proteinase K could digest 12.5 μg of affinity purified lectin with a prolonged 37° C. incubation of 48 hours. With proteinase K under the above conditions, significant HA activity remained. Similar results were obtained with media-derived lectin although the results in this case could be partially explained by the presence of serum proteinase inhibitors in the growth medium.

During the purification procedure sialidase activity was found in all fractions examined in culture fluid. The fact that both the YM-100 flow-through and concentrate contain enzyme activity indicate that two different enzymes, one <100 kD and one of greater MW, may be present. Two different sialidases (referred to as Type I and II) have been reported in *T. foetus;* with MW of 320 and 38 kD, respectively (Crampen et al., *Hoppe Seyler's Z. Physiol.* 360:1703–1712 (1979)).

It is not without precedent that a parasitic organism which inhabits a mucosal environment would possess sialidase activity, which could be involved in adhesion and/or internalization of sialoglycoproteins for penetration, phagocytosis, or other function. Sialidase in association with hemagglutinins specific for sialic acid are found in myxoviruses and paramyxoviruses (Markwell, In: Mirelman (ed.), *Microbial Lectins and Agglutinins: Properties and Biological Activity*, Wiley, New York (1986)) which infect mucous membranes.

The sialidase(s) from *T. mobilensis* can be separated from HA activity by carefully controlling elution conditions from the affinity column. Further evidence of non-identity between the lectin and the enzyme is the fact that they are differentially inhibited by the sialidase inhibitor 3-dehydro-2-deoxy-N-acetyl-neuraminic acid. Affinity purified lectin is not inhibited at inhibitor concentrations up to 100 mM, while the sialidase activity associated with the column is inhibited by 50% at 1 mM inhibitor. These results may suggest the possibility of interactions between the enzyme and the lectin. Alternatively, they may simply reflect the affinity of the sialidase for mucin.

In summary, these and earlier studies provide evidence for the presence in *T. mobilensis* of three components, which, in other parasitic organisms, are independently associated with attachment and invasion: 1) a cytotoxin with thiol proteinase related properties, 2) a surface adhesin and related soluble sialic acid specific lectin and 3) at least one or more sialidases. *T. mobilensis* infection likely involve all these components.

EXAMPLE 3

Purification of *T. mobilensis* Sialic Acid Binding Lectin from Culture Fluid

Culture fluid in which *T. mobilensis* organisms were cultured was collected and the organisms removed by centrifugation. Lectin containing material was precipitated by overnight incubation with 50% (v/v) denatured alcohol at −20° C. The precipitate was collected by centrifugation at 2000×g for 20-30 min. The pellet was redissolved in 0.25% trypsin solution (tissue culture grade) and incubated at room temperature overnight. This treatment took advantage of the extreme resistance of the lectin to trypsin digestion.

The lectin was concentrated by ultrafiltration using an Amicon YM-100 membrane filter. The retentate was stored frozen at −20° C. Lectin activity was tested by hemagglutination as described above. The number of units of HA activity derived from culture medium is strain specific and can be as much as three times of the amount extracted from the organisms (see Example 3, above) grown in the same volume of medium. Thus spent medium serves as a practical source for the isolation of the trichomonad lectin.

EXAMPLE 4

Adherence and Surface Properties of Tritrichomonas Mobilensis, An Intestinal Parasite of the Squirrel Monkey The recently described squirrel monkey intestinal flagellate, *Tritrichomonas mobilensis*, can be enteroinvasive in its host and can penetrate into deep tissues with lethal results in experimentally infected mice (Culberson et al., *J. Parasitol.* 74:774–780 (1988)). The protozoan is also cytopathic in tissue culture (Pindak et al., *Am. J. Primatol.* 9:197–205 (1985); Pindak et al., *J. Clin. Micro.* 25:609–114 (1987)). Herein is reported an initial characterization of the cell surface of the parasite and its adhesiveness to mucosal and tissue culture cells.

A. MATERIALS AND METHODS

1. Separation of monkey intestinal mucosal material

The entire cecum and colon of an adult squirrel monkey, obtained at necropsy, were sectioned longitudinally and washed thoroughly with Hanks' balanced salt solution (HBSS). Mucosal surfaces were gently scraped with a scalpel and the viscous material thus removed was vigorously vortexed for about 2 min and washed thrice by low speed centrifugation (400 g, 5 min). The resulting pellet of epithelial fragments and small pieces of amorphous mucus was resuspended in 1 ml of HBSS.

2. Observation of trichomonad interactions with monkey intestinal mucosal epithelium and mucus PBS-washed parasite suspension was adjusted to a concentration of $3 \times 10^6$/ml. Equal volumes (100 μl) of trichomonads and mucosal material were incubated in microfuge tubes. At various time intervals, wet mount preparations were examined by light microscopy; smears were also prepared for Giemsa staining.

3. Evaluation of parasite adherence to tissue culture cells

Chinese hamster ovary (CHO) cells were chosen because they have been used extensively in cytopathologic studies involving other protozoa that adhere to epithelium, i.e., *Entamoeba histolytic* (Ravdin et al, *J. Clin. Invest.* 68:1305-1313 (1981); Li et al., *J. Exp. Med.* 167:1725-1730 (1988)) and *Trichomonas vaginalis* (Kreiger et al, *Infect. Immun.* 50:778-786 (1985)). Cell cultures were grown in M-199 medium supplemented with 10% fetal bovine serum, penicillin and streptomycin.

The kinetics of *T. mobilensis*-CHO trypsin-dispersed cell interactions were studied in a cell suspension system. Equal volumes (100 μl) of $10^5$ CHO cells and $10^6$ (unless otherwise specified) trichomonads resuspended in serum-free M199 were mixed in microfuge tubes and incubated at room temperature (unless otherwise stated) with gentle agitation. Periodically the percentage of CHO cells with adherent flagellates was determined microscopically in wet-mount preparations, 100 CHO cells being examined in each preparation.

4. Trichomonad-erythrocyte attachment assay

Type O human erythrocytes were washed three times with PBS diluted to 10% suspension and stored at 4° C. for a maximum of 3 days. Sialidase-treated red blood cells were prepared using 0.150 U of *Vibrio cholera* sialidase per ml of red cell suspension in barbital-buffered saline (Paulson et al., *Methods in Enzymology* Vol. 138, Academic Press, NY, pp. 162-168 (1987)). Removal of terminal sialic acid from erythrocyte membranes was tested by microtiter plate hemagglutination assay (see Example 1, above) of cells treated and untreated with *Limulus polyphernus* lectin (Sigma Chemical Co., St. Louis, Mo.) at a concentration of 10-100 μg/ml. Treated erythrocytes were not agglutinated even in the presence of 100 μ/ml of lectin. The PBS-washed erythrocytes were also treated with trypsin (Type III, I mg/ml) or papain (1 mg/ml) (both obtained from Sigma) for 30 min at 37° C. Following treatment, erythrocytes were washed three times with PBS.

Hemagglutination assays with live flagellates were performed as recently described for *Giardia lamblia* (Farthing et al., *Infect. Immun.* 51:661-667 (1986)).

5. Carbohydrate inhibition

Carbohydrates (Sigma) were dissolved in PBS (for HA inhibition study) or in serum-free M-199 (for *T. mobilensis*-CHO cell adherence test) and their pH was adjusted to 7.2 with 0.1M NaOH. The trichomonads were preincubated at room temperature for 15 min in serially-diluted inhibitor sugars before being assayed for attachment to erythrocytes (HA) or CHO cells. All inhibition experiments were performed at least three times.

6. Adherence of enzyme-treated trichomonads

For testing sensitivity of parasite adherence to protease treatment, washed flagellates ($2 \times 10^6$/ml) were exposed to trypsin (Type III, Sigma) at a concentration 1-5mg/ml at 37° C. for 5 to 30 min. Treatment of trichomonads with neuraminidase was performed using 0.5 U of enzyme/ml of suspension. The enzyme-treated protozoa were washed twice with PBS and their viability (as judged by motility) was confirmed by microscopic examination. Adherence and HA capacity of treated trichomonads was assayed as described above.

7. Lectin agglutination

Agglutination of live *T. mobilensis* with lectins with various carbohydrate binding specificities was performed by a slide agglutination assay. Lectin Kit LK-2000 (Vector Laboratories) consisted of the following lectins: concanavalin A (ConA), wheat germ agglutinin (WGA), soybean agglutinin (SBA), gorse seed agglutinin (UEA-1), castor bean agglutinin type 1 (RCA-1), peanut agglutinin (PNA), and horse gram agglutinin (DBA). *Limulus polyphemus* lectin (LPA) was obtained from Sigma, and *Limax flavus* (LFA) agglutinin from EY Labs. Lectins and specific carbohydrates were dissolved in buffers recommended by the manufacturers. Twenty five μl of washed *T. mobilensis* (about $2 \times 10^7$/ml) were placed onto a glass slide. An equal volume of lectin (200 μg/ml) or lectin with specific carbohydrate (final concentration, 100 mM) was added. After mixing for 2 to 3 min, the agglutination was evaluated under a microscope. Prolonged incubation of slides (moist chamber for 30 min) gave comparable results.

8. Electron microscopy

Cultures of *T. mobilensis* in exponential phase growth in TYM medium were pelleted by centrifugation ($800 \times$ g, 5 min), washed three times with PBS, and fixed in 1% glutaraldehyde - 4% formalin in PBS, pH 7.2 for 2 h at 4° C. After fixation the cells were washed twice with PBS, post-fixed with 1% $OsO_4$, dehydrated in ethanol, and embedded in Polybed 812 (Polysciences, Inc.). Ultrathin sections, cut on LKB Ultratome V, were stained with uranyl acetate and lead citrate and examined in a Zeiss EM 109 electron microscope, 80 kV.

B. RESULTS

Adherence of Tritrichomonas to monkey intestinal mucosa and mucus

Parasites (maintained in culture for several years) adhered in vitro to fragments of intestinal epithelium and cell-free mucus. Motile flagellates started to attach to intestinal material immediately after being added to the preparation; after 5-15 min the trichomonads completely coated tissue and mucus fragments. The flagellates had a tendency to adhere first with the posterior end, and later with the lateral side allowing free movement of locomotory organelles. Organisms attached to mucus formed pseudopod-like projections from the posterior end.

2. Interaction of parasites with tissue culture cells

A modified attachment assay with trypsin-dispersed CHO cells (Ravdin et al., *J. Clin. Invest.* 68:1305-1313 (1981)) was used in the evaluation of kinetics and nature of *T. mobilensis* cytoadherence. Motile trichomonads attached readily to CHO cells suspended in serum-free medium. Initial adherence with the posterior end was typical. It was concentration- and time-dependent, but did not depend on temperature (4°, 25° or 37° C.) or pH (pH 5-pH 8).

3. Attachment of flagellates to human erythrocytes

Live trichomonads cause extensive hemagglutination, binding over the entire surface of erythrocytes. Hemagglutinating titer of trichomonads (about $5 \times 10^7$/ml PBS) was consistently 1:8 to 1:16 when tested at 4°, 25° or 30° C. Treatment of red blood cells with trypsin, or papain (which in some instances increases HA by microbial agglutinins (Farthing et al., Infect. Immun. 51:661-667 (1986); Pindak et al., (1986); Sharon, N., The lectins: properties, functions, and applications in biology and medicine, Academic Press, Inc., Orlando, pp. 494-522 (1986)), had no effect on T. mobilensis-mediated HA. Carbohydrate competition studies were therefore performed with normal erythrocytes at room temperature. Among 17 sugars (concentration up to 100 mM), only sialic acid (N-acetylneuraminic or N-glycolylneuraminic acid) and sialyllactose (N-acetylneuraminic acid-lactose) inhibited the 4. Carbohydrate inhibition of trichomonad adherence to CHO cells Inhibition of trichomonad-mediated HA by sialic acid suggested involvement of surface lectin in cytoadherence. This possibility was evaluated in T. mobilensis-CHO cell suspension assay. As above, attachment of the parasites to CHO cells was inhibited by sialic acid and sialyllactose in a concentration-dependent manner. The presence of other carbohydrates, in concentrations up to 100 mM had no effect on attachment of the flagellates to CHO cells.

5. Effect of enzymatic treatment on parasite adherence Pretreatment of trichomonads with trypsin (up to 5 mg/ml, 30 min) or neuraminidase (0.5 U/ml, 30 min) did not affect their binding properties to CHO cells or erythrocytes.

6. Ultrastructure of the glycosylated trichomonad surface membrane

The surface membrane of T. mobilensis cultivated for prolonged periods was found to consist of a single bilayer with patches of electron dense cell coat similar to that of other trichomonads (Honigberg, in: Kreier (ed), Parasitic Protozoa, Academic Press, NY, vol. 2, pp. 275-454 (1978)). Large numbers of ConA, WGA UEA-I and RCA-I-binding site were detected on the trichomonads (Table 7). The lack of agglutination with two sialic acid-binding lectins (LPA, LFA) indicate the absence of sialyl residues on T. mobilensis.

C. DISCUSSION

The results show that the binding characteristics of the monkey flagellates are closer to those described for Giardia lamblia (Farthing et al, Infect. Immun. 51:661-667 (1986)); Inge et al, J. Clin. Pathol. 41:388-392 (1988)) than to those reported for the urogenital human trichomonads T. vaginalis (Krieger et al, Infect. Immun. 50:778-786 (1985)). T. mobilensis attaches to target cells at both 30° and 4° C. Adhesin(s) with lectin properties comparable to those reported from E. histolytica and G. lamblia, are involved in cytoadherence of the monkey trichomonads.

TABLE 7

| Agglutination of Live T. mobilensis by Lectins | | |
|---|---|---|
| Lectin | Carbohydrate specificity | Agglutination[a] |
| ConA | Mannose, Glucose | 3+ |
| WGA | N-Acetylglucosamine | 3+ |

TABLE 7-continued

| Agglutination of Live T. mobilensis by Lectins | | |
|---|---|---|
| Lectin | Carbohydrate specificity | Agglutination[a] |
| UEA-1 | Fucose | 3+ |
| RCA-1 | Galactose | 3+ |
| SBA | N-Acetylgalactosamine | 1+ |
| DBA | N-Acetylgalactosamine | 0 |
| PNA | Gal (β1-3) GalNAc | 0 |
| LPA | N-acetylneuraminic acid | 0 |
| LFA | N-acetylneuraminic acid | 0 |

[a]Scoring: 1+ to 3+, minimal to very strong (almost all cells clumped) agglutination in slide agglutination assay; 0, no agglutination observed, Mannose, N-acetylglucosamine, fucose, galactose and N-acetylgalactosamine (100 mM) abolished agglutinating activity of the appropriate lectins. The final concentration in the assay was always 100 μg/ml.

Attachment of T. mobilensis to CHO cells and erythrocytes is inhibited by sialic acid rather than by glucose/mannose or N-acetyl-galactosamine/galactose, the carbohydrates recognized by surface lectins of G. lamblia and E. histolytica, respectively. Microorganisms may express more than one cell surface lectin-like compound (Ravdin et al., In: Ravdin JT (ed) Amebiasis: Human Infection by Entamoeba histolytica John Wiley & Sons, Inc., USA, pp. 205-218 (1988); Sharon, The Lectins: Properties, Functions, and Applications in Biology and Medicine, Academic Press, Orlando, pp. 494-522 (1986)). That adhesin(s) interactions of T. mobilensis is not directed solely by sialic acid is indicated by hemagglutination of sialidase-treated erythrocytes by live flagellates. Inhibitory studies with various glycoconjugates should further clarify the binding specificities of surface lectin(s) of this trichomonad.

Strains of T. mobilensis which do not attach to CHO cells and erythrocytes but release into culture fluid a hemagglutinin inhibited by sialic acid have recently been isolated (Pindak et al., J. Clin. Micro., J. Clin. Micro. 25:609-114 (1987), Pindak et al., J. Clin. Micro 26:1460-1463 (1988)). Trichomonads with differential cytoadherence as well as CHO cells with enzymatically or genetically modified plasma membrane (Li et al., J. Exp. Med. 167:1725-1730 (1988)) may be useful in further characterizing adherence properties of the intestinal trichomonad from monkeys and in delineating the involvement of adherence in cytopathogenicity.

EXAMPLE 5

Monoclonal Antibodies to a Sialic Acid Binding Lectin

METHODS:

The cloning procedure was a modification of a published procedure (Baum, K. F., et al, J. Parasit. 74:267-269 (1988)). Organisms were diluted and cloned in conditioned TYM media collected from a 24-hour culture. This media was adjusted to pH 7.0, filter sterilized (0.2 μ), and mixed 1:1 with fresh TYM. Dilutions for cloning were made as described in the above-mentioned reference and repeated once for a 99.9% level of certainty of derivation from a single organism. CLones were derived from both ATCC strains. That derived from ATCC: 40597 was designated as clone 4190-5D. Two clones were derived from ATCC: 50011 and were designated as clones 776-7C and 776-5A.

S-35 Labeling of Protozoa

Protozoa were grown in TYM medium to a density of $5-6 \times 10^6$. The culture growth was centrifuged at 1500 rpm for 20 min at 4°. The cell pellets were washed twice with sterile PBS, and spun down as described above. Pellets were suspended in methionine deficient MEM without serum and spun down again. Pellets were suspended in MEM with 5% FCS at a density of $2.5 \times 10^8$ total cells in a volume of 60 mL. After a two-hour incubation at room temperature, 1 mCi of $^{35}S$ radiolabeled methionine (specific activity 1000 Ci/mmol) was added to each flask. Cultures were incubated at 37° C. for 19 hours. The cells were then spun down and washed three times in PBS as described above. Cell pellets could be frozen at −70° or immediately extracted with NET buffer containing protease inhibitor (see protocol immediately below). Extraction buffer was added to give a final cell density of $2.0 \times 10^8$/mL. The suspension was incubated at 4° for 30 min then centrifuged for 10 min at $15,000 \times g$. The supernatant was stored at −70° C. until use.

Solid Phase Immunoisolation Technique (SPIT)

The assay represents a composite of a number of procedures used in various labs. See Chen, C.-L. H., et al., *Eur. J. Immunol.* 14:385-391 (1984). The Hyclone mouse monoclonal sub-isotyping kit was used for plate coating solution and secondary antibody (Hyclone Laboratories, Inc., Logan, Utah).

Day 1: Prepare plate coating solution and use to dilute goat antimouse immunoglobulins solution (2° antibody) as described in the Hyclone kit instructions. Add 200 μL of this antibody solution to each well of a multiwell plate. Incubate overnight at 4°. Plates should be sealed and can also be shaken out, allowed to air dry and resealed for storage at 4° for several weeks after the overnight incubation.

Day 2: Wash wells 3 times with 200 μL of washing buffer (kit supplied PBS+surfactant). Add 200 μL of ascites control (Sigma) or monoclonal antibody-containing ascites diluted 1:10 in PBS+0.2% $NaN_3$. Incubate overnight at 4°.

Day 3: Wash wells 3 times as above. Add 200 μL of mouse serum diluted 1:100 in washing buffer. Incubate two hours at 4° and wash 3 times with washing buffer. Add labeled extract. Up to 200 μL of extract can be added to each well. If sialic acid is used to block lectin-sialoglycoprotein interaction, 33 μL of a 100 mM solution of N-acetylneuramine acid can be added to the extract with thorough mixing before addition to the well. Incubate overnight at 4°.

Day 4: Wash wells 4 times with the same buffer used for cell lysis. For protozoal extracts, NET buffer (0.5% nonidet P-40, 0.15 m NaCl, 5 mM EDTA, 40 mM Tris pH 7.0, and 0.2% $NaN_3$) containing 0.7 μg of pepstatin, 0.5 μg of leupeptin and 33.3 μg of PMSF per mL was used. Add 80 μL of Laemmli SDS sample buffer with 2-mercaptoethanol. Incubate for 2 hours at 37° C. Forty μl will fill the sample well of a 1.5 mm thick Hoefer minigel. An aliquot of the remaining sample can be counted in a scintillation or gamma counter.

Electrophoresis

For preparation and silver staining of the minigels, we use the methods given in Ausubel, F. M., et al. (eds.), In: *Current Protocols in Molecular Biology*, John Wiley & Sons, New York (1989). The silver staining is a modification of Oakley et al., *Anal Biochem.* 105:361-363 (1980). A further modification of that procedure, described by Dubray et al. in *Anal Biochem.* 119:325 (1982) utilizes periodic acid for cleavage of 1,2-diol groups in saccharide units which are then detected by ammonicial silver as described by Oakley but without the gluteraldehyde fixing step.

For protozoal samples, 40 μL of sample was added to the sample wells of a 1.5 mm Hoefer minigel system set up for denaturing polyacrylamide gel electrophoresis in 5% or 7.5% separating gel and 3% stacking gel prepared by the procedure of Laemmli. After electrophoresis, gels were fixed in 50% methanol, 10% acetic acid, 40% $H_2O$ overnight and silver-stained using a modified Oakley procedure. Gels were photographed, then placed in water and FLUORHANCE$^R$. Gels dried on whatman 3M filter paper were placed in a cassette in contact with Kodak XAR-5 film for one week at −70° C. before development. Details of the gel electrophoresis procedure and silver staining methods are found in Current Protocols in Molecular Biology, Vol. 11, chapter 10.

RESULTS AND DISCUSSION

Production of Monoclonal Antibodies

Monoclonal antibodies to mucin-sepharose 4B-purified lectin derived from *T. mobilensis* strain 4190 (ATCC: 40597) were produced by published methods (D. E. Burgess, *Exper. Parasit.* 62:266-274 (1986), herein incorporated by reference) and harvested as ascites fluid. Initial studies were performed by SPIT to determine if these monoclonals could be used to purify lectin from whole organism extracts.

SDS denaturing polyacrylamide gel electrophoresis (7.5%) was performed on SPIT assay material as described above. Silver strains of the gel revealed five high molecular weight (>205 kDa) bands of identical electrophoretic mobility for all five monoclonals. The use of S-35 labeled cell extracts in the SPIT assay followed by PAGE and fluorescence autoradiography demonstrated band patterns identical to those indicated above. No lower molecular weight bands were observed in these autoradiographs indicating that the lectin is a multimer composite of only these high molecular weight subunits.

All five monoclonals inhibited hemagglutination when tested in the inhibition assay described earlier. The inhibition titer is defined by the MAb containing ascites dilution which results in the complete inhibition of two units of HA activity. These titers vary from a low of 1:160 to 1:10,000 with ascites control (Sigma) never inhibiting at dilutions greater than 1:20.

Differences in Lectin and Adherence Properties by Cloned Organisms

HA activity from three cloned organisms was extracted as previously described. The lectin activity obtained from 4910-5D exhibits identical sialic acid binding properties to those obtained for lectin from the parent strain. This clone-derived lectin did not agglutinate neuriminidase-treated erythrocytes. The HA activity derived from clone 776-5A was also inhibited by sialic acid but, in contrast to the 4190-derived lectin, agglutinated neuraminidase- treated erythrocytes although to a much lesser extent than non-treated. Residual sialic acid on the enzyme-treated RBCs was not responsible for this latter observation because such HA activity was not inhibited by sialic acid at concentrations far in excess of those needed to inhibit lectin from 4190-5D.

The 776-7C clone has been examined for HA activity. No erythrocyte agglutinating activity was found in the whole organism extracts. Cultures of this clone grown in FP media also did not produce any detectable lectin activity in the media using the HA assay.

Whole organism extracts of both 776 clones as well as T. foetus strain have been checked for immunocrossreactivity with a monoclonal antibody which inhibits HA activity of 4190 lectin at a dilution of 1:10,000. A SPIT assay performed with NET buffer extracts of S-35 methionine labeled organisms (described elsewhere) revealed high molecular weight banding patterns that were unique for 4190-5D, 776-5A and T. foetus. Although all organisms examined had nearly equal specific activities (cpm/mg protein), the 776-7C clone never demonstrated any autoradiographically detectable bands. These results, taken together with the absence of any HA activity in this clone, demonstrate that no functional or immunologically recognizable lectin is present in this clone.

Tritrichomonas mobilensis, an enteric parasite of squirrel monkeys, adheres readily to isolated monkey intestinal epithelial cells and agglutinates human erythrocytes in vitro. These activities are mediated by a sialic acid binding lectin. Hemagglutination by either parasites or purified lectin is inhibited by N-acetylneuraminic acid and anti-lectin monoclonal antibody (MAB), but not by 2,3-dehydro-2-desoxy-N-acetylneuraminic acid, a neuraminidase inhibitor. T. mobilensis hemolyzes erythrocytes in a modification of a previously published whole organism hemolysis assay. Hemolysis is inhibited by N-acetylneuraminic acid, 2,3-dehydro-2-desoxy-N-acetylneuraminic acid, anti-lectin MAB, T. mobilensis lectin and other sialic acid binding lectins, fetuin, and colominic acid, but not by asialofetuin, or leupeptin. Desialated erythrocytes are neither agglutinated nor hemolyzed.

These data suggest that T. mobilensis cytolytic activity is a complex process involving cofunction of lectin, neuraminidase, and other, as yet undefined, lytic enzymes.

EXAMPLE 6

Glycoprotein staining with the T. mobilensis lectin isolated from the ATCC:40,597 strain is not affected by fixation with formalin, acetone, and ethyl or methyl alcohol. There are no basic differences in staining between cryostat and formalin-fixed paraffin sections. Cytoplasmic staining is more readily expressed in frozen specimens. However, formalin fixed specimens display better demarcated positivity and grant more precise morphological localization. The histochemical procedure includes 60–90 minutes incubation of the lectin at a concentration of 5–10 μg/ml in PBS, pH 7.2; application of 2% nonfat dry milk in PBS as an inhibitor of nonspecific binding of anti-lectin monoclonal antibodies; and 30 minute incubation with primary anti-lectin mouse monoclonal antibodies (clones 10C4 or 7C3 produced in our department) diluted 1:800 in PBS. The rest of the staining procedure is an application of the Vectastain ABC kit (Vector Laboratories, Burlingame Calif., USA) according to the manufacturer's instruction. The endogenous peroxidases are neutralized in a 10 minute bath of 0.05% $H_2O_2$ in PBS prior to ABC complex application. The histochemical staining of the lectin can be blocked by sialic acid or by treatment of the tissue sections with neuraminidase.

The most prominent lectin staining appears to be the glycocalyx of the glandular structures, followed by the luminal surfaces of transitional epithelium, glomerular podocytes, vascular endothelium, amniotic lining and trophoblast. Membranous reactivity is seen on some glandular cells (breast, sweat glands); on basal cells of transitional epithelium and squamous epithelia (skin, vagina, pharnyx, esophagus), on erythrocytes, polymorphonuclear leukocytes, macrophages and some lymphocytes. Fine granular cytoplasmic staining can be found in most parenchymal organs (salivary glands, pancreas, tubular epithelium of kidney, liver), in decidual cells, in the white matter of brain and in some endothelial cells. Mucin of the gastrointestinal tract can be stained only by using 2–3 fold higher concentrations than that used for the above-mentioned studies. Almost no staining of mucin is found in the salivary glands, pancreas, stomach; moderate staining is found in the cervical cells, respiratory epithelium and ovarian mucin; better staining is obtained by the mucin of the gall bladder and that of colonic mucosa. In connective tissues, fibroblasts show cytoplasmic and some level of membrane reactivity. Slight membrane reactivity can also be observed on lipocytes.

The Tritrichomonas mobilensis lectin shows some differential staining in glycosylated proteins of tumor tissues. However, staining of endothelial cells is consistent, even in tumors derived from endothelium. These properties of the lectin can also be of some diagnostic value.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of identifying a lectin-binding region in a histological preparation comprising the steps of:
    (a) incubating a tissue section or cell preparation with a sialic acid-binding lectin isolated from a species belonging to the genus Tritrichomonas, substantially free of natural contaminants, or a polypeptide subset of the intact lectin molecule which retains the function of binding to sialic acid, substantially free of natural contaminants;
    (b) washing said tissue section or cell preparation to remove unbound material;
    (c) additionally incubating said tissue section or cell preparation with detectably labeled lectin-binding material; and
    (d) detecting bound detectably labeled lectin-binding material to visualize tissue- or cell-bound lectin.

2. The method of claim 1 wherein lectin-binding material of step (c) is selected from the group consisting of sialic acid, polysialic acid, sialic acid-containing polysaccharide, and sialoglycoproteins.

3. The method of claim 2 wherein said sialoglycoprotein is fetuin.

4. The method of claim 1 wherein said detectable label in step (c) is selected from a group consisting of enzyme labels, radioisotopic labels, non-radioactive isotopic labels, fluorescent labels, toxin labels, and chemiluminescent labels.

5. The method of claim 1 wherein said lectin-binding material is fetuin and said detectable label is colloidal gold.

6. The method of claim 1 wherein said tissue section or cell preparation contains a cancer cell.

7. The method of claim 1 wherein said tissue section or cell preparation contains a lymphocyte.

8. The method of claim 7 wherein said lymphocyte is of human origin.

9. A method for detecting the presence of sialic acid either free or associated with larger molecules in a biological fluid, comprising contacting said sialic acid-containing biological fluid with a detectably labeled sialic acid binding lectin isolated from a species belonging to the genus Tritrichomonas, or a detectably labeled polypeptide subset of the intact lectin molecule which retains the function of binding to sialic acid, and detecting binding of said sialic acid to said lectin or to said polypeptide subset of said lectin.

10. The method of claim 9, wherein unlabeled sialic acid-binding lectin isolated from a species belonging to the genus Tritrichomonas, or a polypeptide subset of the intact lectin molecule which retains the function of binding to sialic acid is attached to a solid support, the sialic acid is allowed to bind to said solid support, and the presence of said sialic acid is detected by detecting said detectably labeled lectin or said detectably labeled polypeptide subset of said lectin.

* * * * *